(12) United States Patent
Kroll et al.

(10) Patent No.: US 7,756,577 B1
(45) Date of Patent: Jul. 13, 2010

(54) MULTI-MODAL MEDICAL THERAPY SYSTEM

(75) Inventors: Mark W. Kroll, Crystal Bay, MN (US); Euljoon Park, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 1118 days.

(21) Appl. No.: 11/409,380

(22) Filed: Apr. 21, 2006

(51) Int. Cl.
*A61N 1/00* (2006.01)

(52) U.S. Cl. .......................................................... 607/4
(58) Field of Classification Search ...................... 607/4, 607/5, 32; 600/16
See application file for complete search history.

(56) References Cited

U.S. PATENT DOCUMENTS

| | | | |
|---|---|---|---|
| 3,911,898 A | 10/1975 | Leachman, Jr. | |
| 4,210,149 A * | 7/1980 | Heilman et al. | 607/5 |
| 5,222,980 A | 6/1993 | Gealow | |
| 5,383,840 A | 1/1995 | Heilman et al. | |
| 5,935,158 A | 8/1999 | Holmstrom et al. | |
| 5,961,540 A * | 10/1999 | Renger | 607/32 |
| 6,110,098 A * | 8/2000 | Renirie et al. | 600/16 |
| 6,263,241 B1 | 7/2001 | Rosborough et al. | |
| 6,292,694 B1 | 9/2001 | Schloss et al. | 607/9 |
| 6,298,267 B1 | 10/2001 | Rosborough et al. | |
| 6,510,342 B1 | 1/2003 | Park et al. | 607/15 |
| 6,519,493 B1 | 2/2003 | Florio et al. | 607/9 |
| 6,606,517 B1 | 8/2003 | Park et al. | 607/14 |
| 6,694,188 B1 | 2/2004 | Kroll | 607/14 |
| 6,695,761 B2 | 2/2004 | Oschman et al. | 600/16 |
| 6,766,194 B1 | 7/2004 | Kroll | 607/9 |
| 6,775,571 B1 | 8/2004 | Kroll | 607/9 |
| 6,804,556 B1 | 10/2004 | Florio et al. | 607/9 |
| 7,050,849 B2 | 5/2006 | Echt et al. | |
| 2003/0144572 A1 | 7/2003 | Oschman et al. | 600/16 |
| 2004/0260214 A1 | 12/2004 | Echt et al. | 601/46 |
| 2005/0119706 A1 | 6/2005 | Ideker et al. | |
| 2005/0131468 A1 | 6/2005 | Echt et al. | 607/9 |

FOREIGN PATENT DOCUMENTS

| | | |
|---|---|---|
| EP | 1 078 649 A1 | 2/2001 |
| EP | 1078649 A1 | 2/2001 |

(Continued)

OTHER PUBLICATIONS

Hideyuki Honda, M.D. et al., "Mathematical Model of the Effects of Mechanical Vibration on Crossbridge Kinetics in Cardiac Muscle", *Jpn Circ J*, Jun. 1994; vol. 58, pp. 416-425.

(Continued)

*Primary Examiner*—George Manuel

(57) ABSTRACT

A device and methods for automatically evaluating one or more patient physiological parameters and, upon determination that certain therapies are indicated, delivering therapeutic mechanical stimulations to tissue of the patient. The mechanical stimulations generally include vibrations delivered at frequencies somewhat higher or lower than an intrinsic frequency and the therapeutic vibrations are delivered to drive the intrinsic frequency towards a desired value. The device and methods more closely emulate natural physiologic feedback mechanisms and can reduce undesired side effects of other known therapies. The device can include a small and efficient electrical motor which is interconnected with a crank and link mechanism to generate oscillatory motion which is conducted to a flexible wall of a bio-compatible housing of the device.

21 Claims, 14 Drawing Sheets

FOREIGN PATENT DOCUMENTS

| WO | 0113990 A1 | 3/2001 |
|---|---|---|
| WO | WO 01/13990 | 3/2001 |
| WO | 2004112885 A2 | 12/2004 |
| WO | 2004112885 A3 | 12/2004 |
| WO | 2004112886 A2 | 12/2004 |
| WO | WO 2004/112885 A2 | 12/2004 |
| WO | WO 2004/112885 A3 | 12/2004 |
| WO | WO 2004/112886 A2 | 12/2004 |
| WO | WO 2004/112886 A3 | 12/2004 |

OTHER PUBLICATIONS

H. Hsiu, et al., "Influencing the Heart Rate of Rats with Weak External Mechanical Stimulation", *PACE*, Jan. 2003; vol. 26, Part I, pp. 36-43.

Yoshiro Koiwa, MD et al., "Modification of Human Left Ventricular Relaxation by Small-Amplitude, Phase-Controlled Mechanical Vibration on the Chest Wall", *Circulation*, Jan. 1997; vol. 95, No. 1, pp. 156-162.

Yoshiro Koiwa, MD, M.D. et al., "Ventricular Contractility Evaluated by Mechanical Perturbation of the Myocardium—Experimental and Clinical Approach Adopting Small Amplitude Vibration Input", *Jpn Circ J*, Jul. 1992; vol. 56, pp. 735-739.

Takehiko Nishioka et al., "Mechanoenergetics of Negative Inotropism of Ventricular Wall Vibration in Dog Heart", *Am J Physiol.*, Feb. 1996; vol. 270 (2 Pt 2):H583-H593.

Takehiko Takagi, MD et al., "Diastolic Vibration Improves Systolic Function in Cases of Incomplete Relaxation", *Circulation*, Dec. 1992; vol. 86, No. 6, pp. 1955-1964.

NonFinal Office Action, mailed Dec. 24, 2008—Related U.S. Appl. No. 11/049,781.

Notice of Allowance, mailed Jun. 17, 2009—Related U.S. Appl. No. 11/049,781.

NonFinal Office Action, mailed Dec. 28, 2007—Related U.S. Appl. No. 11/049,781.

NonFinal Office Action, mailed Jun. 30, 2008—Related U.S. Appl. No. 11/049,781.

NonFinal Office Action, mailed Dec. 28, 2006: Related U.S. Appl. No. 11/049,781.

Final Office Action, mailed Jun. 20, 2007: Related U.S. Appl. No. 11/049,781.

Advisory Action, mailed Sep. 27, 2007: Related U.S. Appl. No. 11/049,781.

* cited by examiner

MULTI-MODAL MEDICAL THERAPY SYSTEM

CROSS-REFERENCE TO RELATED APPLICATIONS

This application is related to co-pending U.S. patent application Ser. No. 11/049,781 filed Feb. 1, 2005, entitled "Indirect Mechanical Medical Therapy System".

FIELD OF THE INVENTION

The invention relates to the field of medical therapy devices and more particularly to devices and algorithms for automatically evaluating and providing indirect mechanical stimulation in combination with electrical stimulation as therapy for tachycardia with improved patient comfort.

BACKGROUND OF THE INVENTION

A large number of people suffer from health conditions which are either directly or indirectly related to their cardiac function. For example, hypertension refers to a chronic disease in which the patient's systemic blood pressure is elevated above that which is considered a healthy level. As a chronic condition, hypertension can contribute to a wide variety of well-known health ailments. Accordingly, therapy for a known hypertension condition is typically prescribed to ameliorate the hypertension condition and related effects. Depending on the severity of the hypertension as well as the patient's individual condition, typical therapies can include diet modification, an exercise regimen, and/or a medication regimen.

Another category of cardiac related health ailments include cardiac arrhythmias. A number of medications are known which can help restore, at least partially, more normal sinus rhythm for certain patients. Another known category of therapy for cardiac arrhythmias includes implantable cardiac stimulation devices, such as pacemakers and/or implantable cardioverter-defibrillators (ICDs). Implantable cardiac stimulation devices automatically monitor the ongoing cardiac activity of the patient and selectively provide direct electrical stimulation to the cardiac tissue when indicated in an attempt to restore the patient's intrinsic rhythm to a sinus rhythm or alternatively to substitute for the patient's intrinsic rhythm and assume control of the heart's activity for at least some period of time, such as in pacing.

One particular health ailment that frequently can be effectively treated with an implantable cardiac stimulation device is paroxysmal atrial fibrillation (AF). AF is a condition of rapid, chaotic atrial contractions that results in much less effective atrial pumping and reduced overall cardiac efficiency. Paroxysmal refers to sudden periodic recurrence or worsening of the AF. AF is not generally life-threatening, however occurrences of AF frequently contribute to further ongoing episodes of AF. AF is also known to increase the risk of thromboembolism and has been associated with heart failure (HF).

An implantable cardiac stimulation device can be provided and programmed to deliver atrial overdrive pacing as therapy for paroxysmal AF. The device is typically programmed to provide atrial pacing stimulation at a rate generally 5-20 pulses per minute (ppm) greater than an intrinsic rate. This atrial overdrive suppresses recurrence of AF episodes. A drawback to this therapy however is that the artificially elevated heart rate induced by the atrial overdrive pacing is irritating to some patients and can disrupt restful sleep.

One possible alternative to providing therapy while avoiding the physiologic drawbacks of overdrive pacing would be to provide some manner of indirect therapy or stimulation, such as provided by the body's natural feedback mechanisms. For example, providing stimulation to the vagus and/or sympathetic nerves has been considered as a possible avenue for therapy delivery. However, it has as yet proven impractical to access these nerves and to realize effective placement of leads on them to provide stimulation on a long-term basis.

Thus, it will be understood that there is an ongoing need for providing interventional therapy in a manner which reduces the negative consequences or side effects of known therapies. There is also a desire for therapy which is relatively inexpensive and simple to implement and also for therapy which more closely emulates natural physiological feedback and response.

SUMMARY

Certain embodiments described herein are at least partially based on the idea that a patient's heart rate is naturally adjusted to match the hydrodynamic impedance characteristics of their arterial system, and that their heart rate is naturally maintained at a frequency so as to utilize these characteristics for increased efficiency and reduced energy expenditure. As the hydraulic or hydrodynamic impedance of the arterial system can be subject to both short term and long term variations, such as by change in the cross-sectional area of a vessel, the elasticity of the arterial wall, the thickness thereof, etc., embodiments of the invention employ the approach of simulating a change in the hydrodynamic impedance characteristics of the arterial system so as to provide a stimulation to drive the heart rate in a desired manner.

In certain implementations, mechanical perturbations are generated and conducted to patient tissue in a synchronized manner to artificially and indirectly steer a pre-treatment intrinsic heart rate to a desired post-treatment intrinsic rate. The mechanical perturbations are provided for at least a selected interval to allow the patient's metabolism to become accommodated to the new intrinsic rate. With a new, lower intrinsic rate, a second mode of therapy, in one implementation electrical pacing stimulation, can be provided to "overdrive" on top of the new, lower intrinsic rate at an actual or effective rate that can be equal or less than the pre-treatment intrinsic rate. The patient can thus receive multiple modes of therapy, including overdrive pacing, which will inhibit certain arrhythmic conditions but without having an actual heart rate that is elevated above the pre-treatment intrinsic rate. The patient receives the benefits of overdrive pacing with reduced discomfort from an elevated heart rate.

DETAILED DESCRIPTION

Reference will now be made to the drawings wherein like numerals refer to like parts throughout. The following description includes the best mode presently contemplated for practicing the invention. This description is not to be taken in a limiting sense but is made merely for the purpose of describing the general principles of the invention. The scope of the invention should be ascertained with reference to the issued claims. In the description that follows, like numerals or reference designators will be used to refer to like parts or elements throughout.

Certain embodiments described herein are based on theories and clinical observations of a hydrodynamic link between cardiac activity and the characteristics of the arterial system. It has been theorized and clinical observations support the idea that the circulatory system can be at least partially modeled by a pressure source (the heart) and a lumped parameter hydraulic impedance, including the arterial system. Pressure waves emanating from the heart, such as upon the ejection of blood upon a contraction, have a wave velocity that can be considered matched to a certain degree with a natural wave velocity of the arterial system. A resonance condition where the cardiac frequency (heart rate) substantially matches the natural frequency of the arterial system can lead to enhanced efficiency of the circulatory transport system. In this resonance model, it is believed that the cardiac output waves can interact with reflected waves in the arterial system in a constructive interference manner so as to increase coronary perfusion. This can lead to an increase in overall circulatory system efficiency and a corresponding reduction in cardiac output energy with improved blood flow throughout the body at reduced blood pressure.

Figure 1:
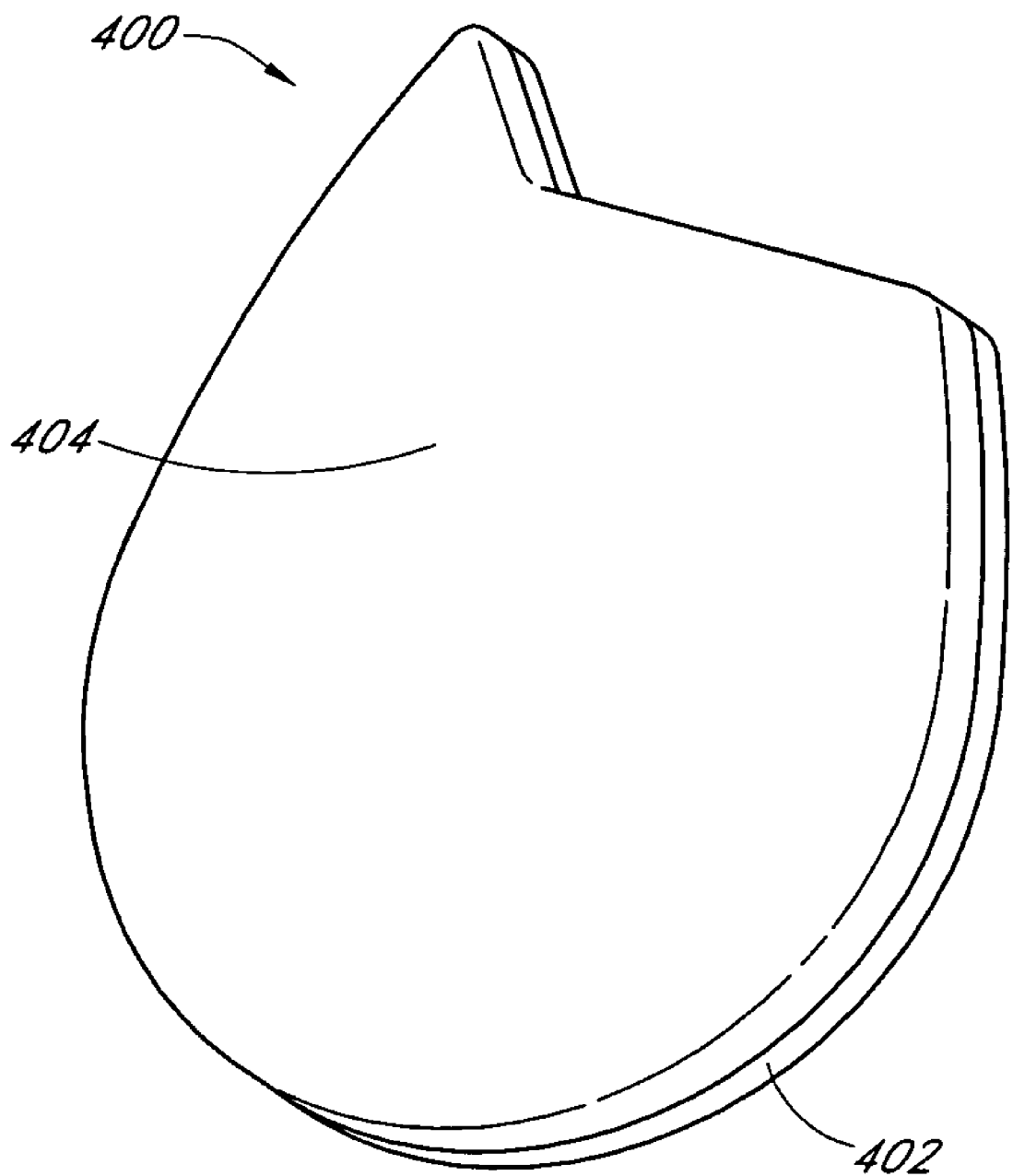
FIG. 1 is a perspective view of one embodiment of a mechanical medical therapy device.

FIG. 1 is a perspective view of an embodiment of a mechanical stimulation device 400 suitable for providing medical therapy. In some embodiments, the mechanical stimulation device 400 is partially or wholly implantable and in other embodiments is configured to be placed and secured in a close proximity to the patient's tissues so as to provide mechanical stimulation thereto. In certain embodiments, the device 400 is adapted to provide mechanical stimulations or vibrations to mimic changes in the hydrodynamic impedance to drive the heart rate higher or lower without requiring direct electrical stimulation. These embodiments will be described in greater detail following a more detailed description of certain embodiments of components and structure of the device 400.

In one embodiment, the device 400 comprises a substantially rigid housing portion 402 as well as a displaceable housing portion 404. The displaceable housing portion 404 is configured such that the device 400 can automatically spatially displace the displaceable housing portion 404 so as to conduct mechanical vibrations to the patient's tissue. In this embodiment, the displaceable housing portion 404 comprises a region of flexible biocompatible material, however, in other embodiments the displaceable housing portion comprises articulated or jointed portions which can move with respect to the rigid housing portion 402.

Figure 2:
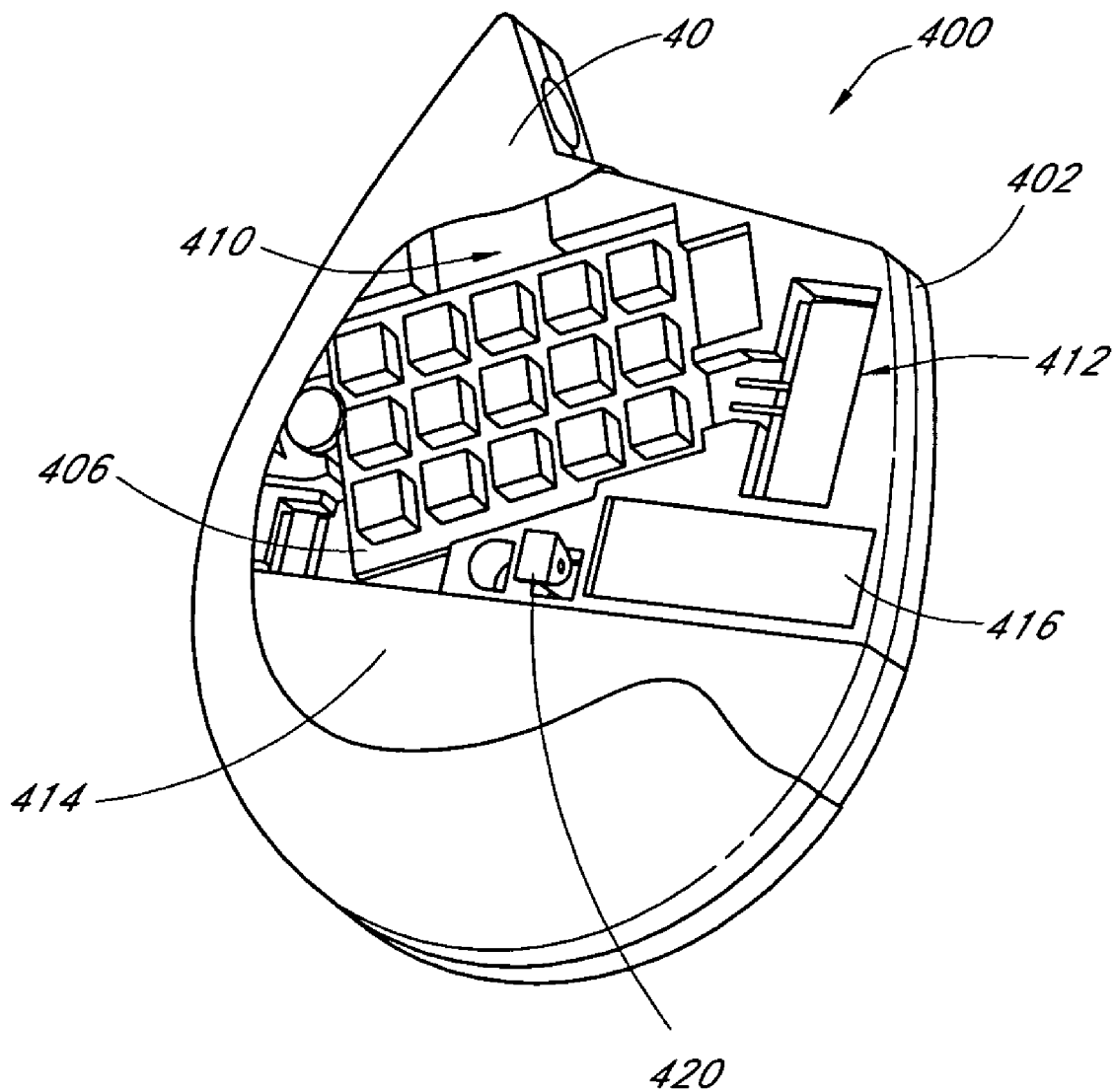
FIG. 2 is a partial cut-away perspective view of an embodiment of a mechanical medical therapy device.

FIG. 2 illustrates in greater detail in a partial cut away perspective view one embodiment of internal components of the mechanical stimulation device 400 configured to selectively provide mechanical therapeutic stimulations. In this embodiment, the device 400 comprises a hybrid electronics assembly 406 which is interconnected to the rigid housing portion 402 via a hybrid support 410. The hybrid electronics assembly 406 determines the timing and control signals for providing mechanical stimulation via the device 400.

The device 400 also comprises a motor 412 which provides rotary motion, preferably in a manner which requires relatively low power consumption as well as in a manner with relatively low levels of electromagnetic interference. A battery 414 is provided which, in this embodiment, provides electrical operating power both to the hybrid electronics assembly 406 as well as to the motor 412.

The rotary output of the motor 412 is conveyed to a displacement mechanism 420, in one embodiment via a gear box or drive mechanism 416. The displacement mechanism 420 is interconnected to the displaceable housing portion 404 such that the displacement mechanism 420 can selectively induce the displaceable housing portion 404 to oscillate or vibrate so as to provide mechanical stimulation to patient tissue via contact with the displaceable housing portion 404. In various embodiments, the displacement mechanism 420 can comprise an eccentric or cam profile, a mechanical linkage arrangement, a hydraulic or pneumatic drive cylinder, and/or a linear actuator, such as an electrical solenoid.

In embodiments including the drive mechanism 416, the drive mechanism 416 can provide gear-up/gear-down functionality so as to provide different rotational velocities between the motor 412 and the displacement mechanism 420. In various embodiments, the drive mechanism 416 can include direct mechanical coupling, such as via bevel, hypoid, worm and/or spur gears/gear trains and in other embodiments the drive mechanism can be an indirect mechanical coupling, such as via pulleys and belt and/or chain and sprockets. In other embodiments, the motor 412 is directly connected to the displacement mechanism 420.

Figure 3:
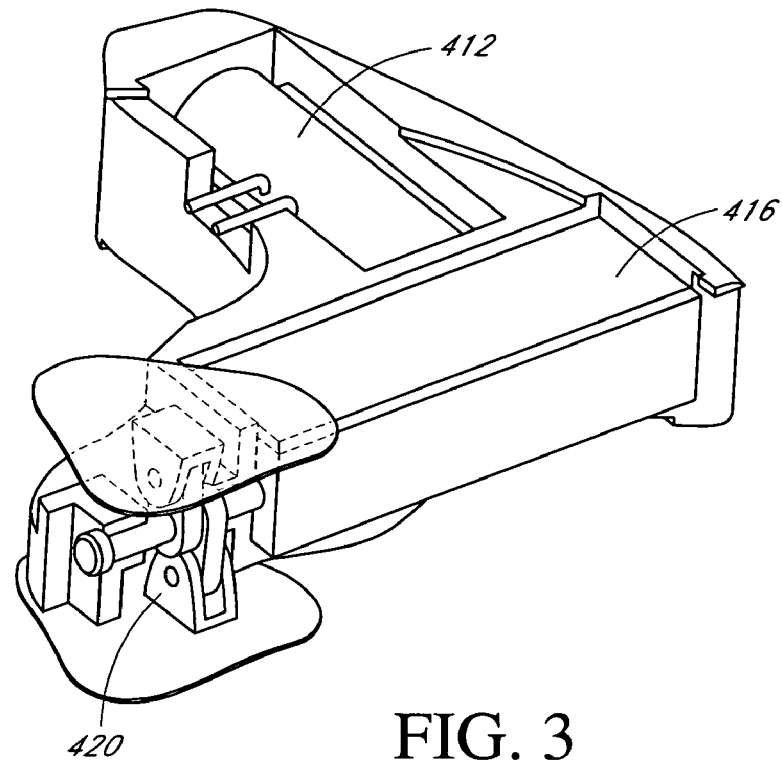
FIG. 3 is a detail of one embodiment of a mechanical displacement system.
Figure 4:
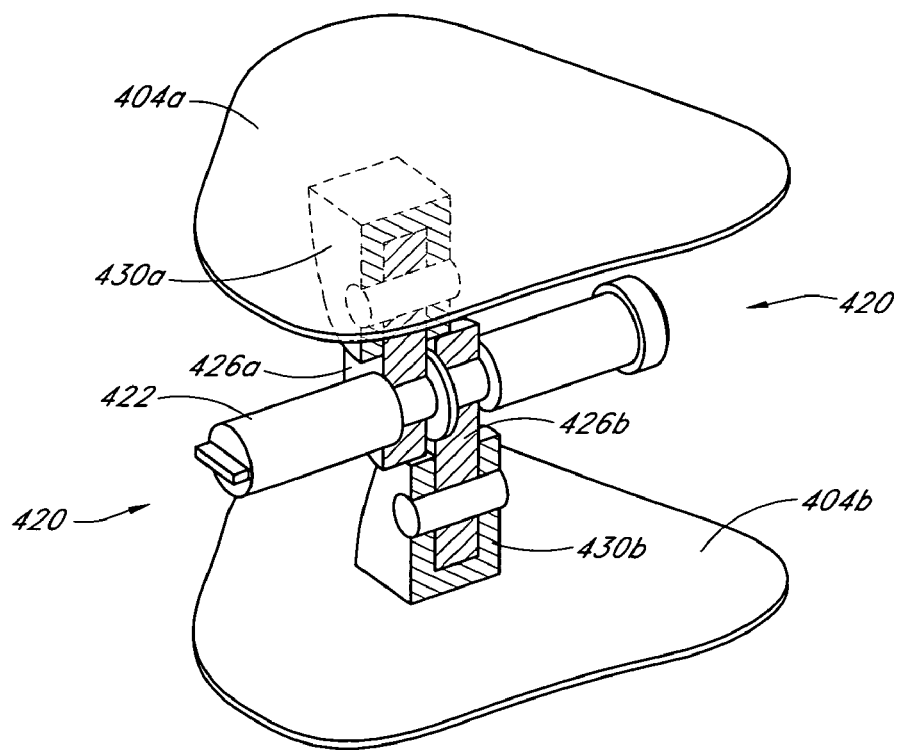
FIG. 4 is a further detail of one embodiment of a displacement mechanism.
Figure 5:
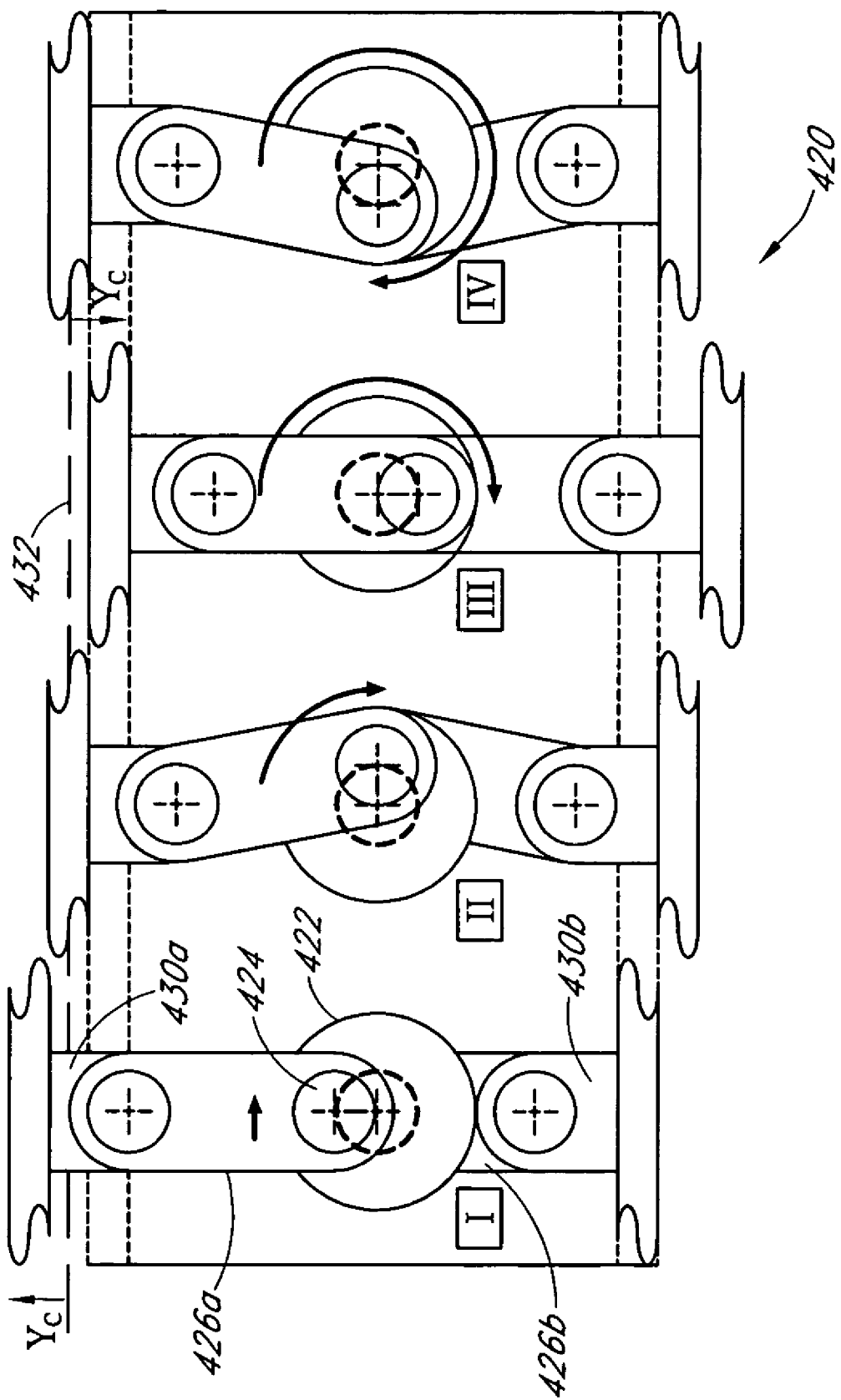
FIG. 5 illustrates an embodiment of operation of the displacement mechanism of FIG. 4.

FIGS. 3, 4, and 5 illustrate in further detail one particular embodiment of a displacement mechanism 420. In this embodiment, the displacement mechanism 420 comprises a drive shaft 422 having one or more, in this embodiment 2, offset crank pins 424. The offset crank pin(s) 424 are arranged with respect to the drive shaft 422 such that rotation of the drive shaft 422 about a major axis thereof will induce the offset crank pin(s) 424 to revolve in a generally circular manner. A first end of corresponding one or more links 426 is connected to the crank pins 424 with an opposite second end of the corresponding links 426 interconnected to a connector 430 which is secured to a portion of the displaceable housing portion 404.

Thus, as can be seen most clearly in FIG. 5, rotation of the drive shaft 422, in this embodiment provided by the rotary motion of the motor 412 as conducted by the drive mechanism 416, induces the crank pin 424 to rotate about a generally circular path and, as the crank pin 424 is interconnected to the link 426 and thus to the connector 430 and displaceable housing portion 404, rotation of the drive shaft 422 induces the corresponding link 426, connector 430 and attached portion of the displaceable housing portion 404 to reciprocate or cyclically oscillate about a neutral position 432.

Thus, the displaceable housing portion 404 is cyclically displaced a distance $Y_c$ from this neutral position 432 thereby providing oscillating vibrations or pressure waves to patient tissue in adjacency with the device 400. In this particular embodiment, the device 400 provides these vibrations or spatial displacements on opposed sides via opposing displaceable housing portions 404a and 404b however in other embodiments the mechanical stimulation may be provided at a single side or location of the device 400 without detracting from the scope of the invention.

Figure 6:
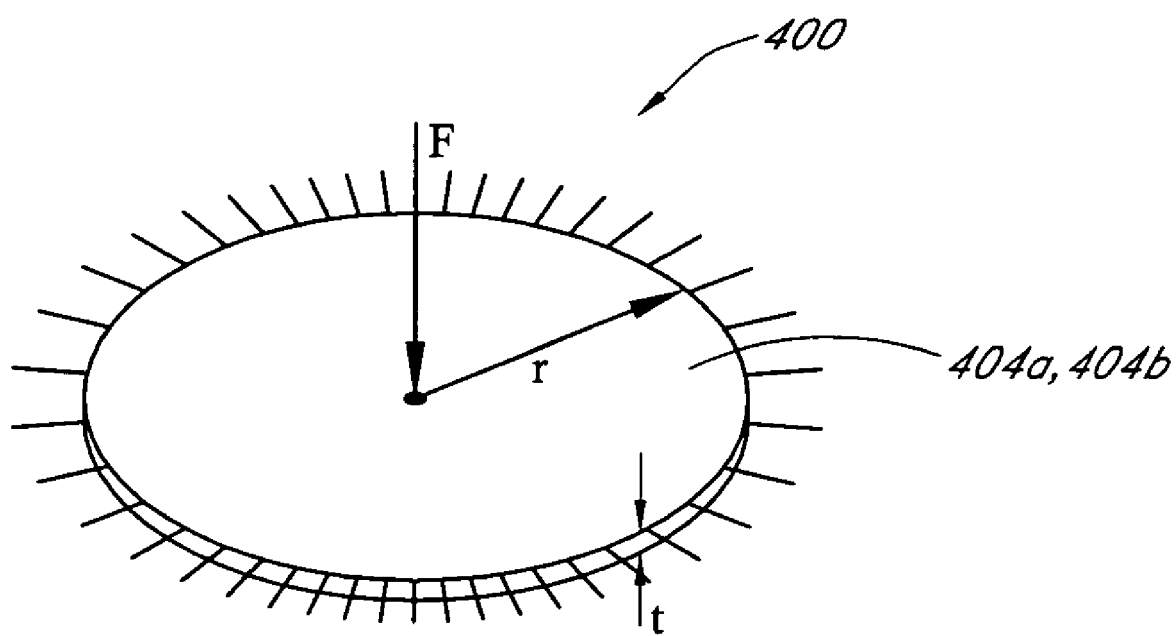
FIG. 6 is a schematic representation of a portion of one embodiment of mechanical stimulation device.

Following is provided a more detailed description with reference to FIG. 6 of one particular embodiment of a mechanical medical stimulation device 400. It will be understood that this is one particular exemplary embodiment and that variations in the dimensions, frequencies, materials, etc. may be appropriate selected for a particular application by one of ordinary skill in the art.

Problem A: It is desired to apply approximately 100 pascals at a frequency of approximately 90 beats or cycles per minute (bpm). The power required is determined as follows:

Assumptions:
Device is modeled as a circular plate with fixed edges
Use maximum elastic modulus for titanium (120 GPa)
Force is applied at center of plate
Neglect mass of plate
Schematic+Given Data:
(FIG. 6)
r=0.01905 m (0.75 in)
t=0.000254 m (0.010 in)
A=0.00114 m² (1.767 in²)
$\wp$=4510 kg/m3 (0.163 lb/in3)
E=120 GPa (17.4×10⁶ psi)
V=0.34
Pr=100 Pa (0.0145 psi)
f=1.5 Hz (90 bpm)
ω=2πf=9.42 rad/$_s$

| Terms: | |
|---|---|
| r—radius | D—flexural rigidity |
| t—thickness | f—frequency |
| A—area | ω—angular frequency |
| $\wp$—density of titanium | $P_o$—power |
| E—elastic modulus | F—force |
| V—Poisson's ratio | $Y_{center}$—deflection |
| P—pressure | |

Flexural Rigidity Calculation:

$$D = \frac{Et^3}{12(1-V^2)}$$

$$D = \frac{(120 \text{ GPa})(.000254 \text{ m})^3}{12(1-0.34^2)}$$

$$D = 0.185 \text{ Nm}(1.640 \text{ lb}_f \text{ in})$$

Analysis
Deflection @ center of plate with 100 Pa applied.

$$y_{center} = \frac{Fr^2}{16\pi D} = \frac{PAr^2}{16\pi D}$$

$$y_{center} = \frac{(100 \text{ Pa})(0.00114 \text{ m}^2)(0.01905 \text{ m})^2}{16\pi(0.0185 \text{ Nm})}$$

$$y_{center} = 4.450 \text{ μm}(0.175 \text{ mil})$$

Power $$P_o = F \cdot y_{center} \cdot \omega$$

$$P_o = (0.114 \text{ N})(4.45 \text{ μm})(9.42 \text{ rad}/_s)$$

$$\boxed{P_o = 4.78 \text{ μW}}$$

Consumption Example 1

| Battery, Lithium Iodine, (WGL 9438) 1120052 | |
|---|---|
| Capacity: 950 mAh | |
| Output: 2.8 Vdc | Energy Available: 2.600 Wh |

Life of Device=

$$\frac{EnergyAvailable}{PowerRequired} = \frac{2.6 \text{ Wh}}{4.78 \times 10^{-6} \text{ W}} = 5.566 \times 10^5 \text{ h}(63.5 \text{years})$$

Design Analysis for Flex Can Drawings

Problem B: The device is to be deflected approximately 0.010" at center at a rate of approximately 90 bpm.

Find: The force and power required are determined as follows.

Assumptions:
same as Problem A
Schematic and Given Data:
same as Problem A
Analysis:
Force @ center of plate with 0.010" of deflection.

$$y_{center} = \frac{Fr^2}{16\pi D}$$

$$F = 16\pi D y_{center}$$

$$F = \frac{16\pi(0.185 \text{ Nm})(0.000254 \text{ m})}{(0.01905 \text{ m})^2}$$

$$F = 6.5 \text{ N}(1.47 \text{ lb}_f)$$

Power $$P = f \cdot y_{center} \cdot \omega$$

$$P = (6.50 \text{ N})(0.000254 \text{ m})(9.42 \text{ rad}/s)$$

$$\boxed{P = 0.01555 \text{ W}}$$

Consumption Example 2

Lithium Iodine Battery
Energy Available: 2.660 Wh $$\text{Life} = \frac{\text{Energy}}{\text{Power}} = \frac{2.66 \text{ Wh}}{0.015555 \text{ W}} = 171 \text{ h}(7.1\text{days})$$

Thus as described above, in one embodiment, the device 400 includes mechanical stimulation components that can provide vibrations of approximately 100 pascals in pressure at approximately 90 bpm corresponding to a net power of approximately 4.8 μW. Assuming 100% energy conversion efficiency, this power could be provided by a standard lithium iodine battery in the device 400 for over 63 years, neglecting other power draws. Thus the device 400 can provide therapy continuously for extended periods of time for treatment of chronic conditions.

In another embodiment, much higher pressure vibrations, such as at approximately 5700 pascals, can be provided for shorter periods, in this embodiment slightly over 7 days, again assuming 100% energy conversion efficiency and neglecting other power draws. The relatively lower pressure vibrations can provide effective therapy for extended periods of time, while significantly higher pressure vibrations can be provided for briefer periods when indicated, for example when it is desired to more rapidly adjust the patient's heart rate/blood pressure.

As previously described, the device 400 can provide therapeutic mechanical vibrations for a variety of patient conditions, including cardiac arrhythmias, however the electrical stimulation capability is not required in all embodiments. Thus, in various embodiments, the device 400 can be configured solely to provide the mechanical therapy described herein as well as the mechanical therapy in combination with electrical stimulation, such as pacing and/or cardioversion/ defibrillation. Depending on the particular application, embodiments can provide a more simplified mechanical therapy device 400 lacking the electrical stimulation capability while providing a simpler, less expensive device 400, for example for treatment of chronic hypertension conditions, as well as other embodiments offering more comprehensive therapy options.

Figure 7:
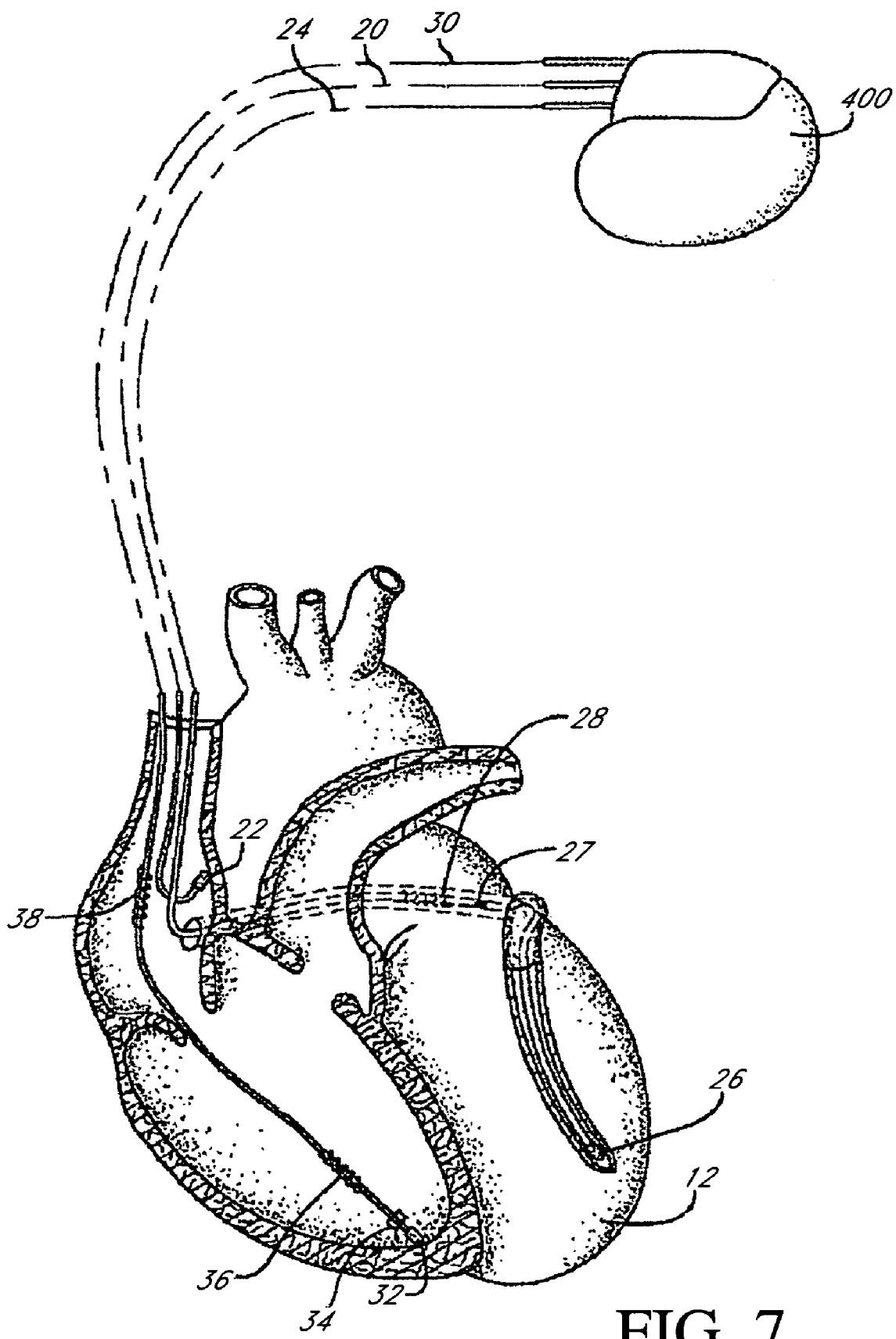
FIG. 7 is a simplified diagram illustrating one embodiment of a mechanical medical therapy device combined with an implantable stimulation device in electrical communication with at least three leads implanted into a patient's heart for delivering multi-chamber stimulation and shock therapy as well as mechanical therapy.

Further description will now be provided of embodiments of a device 400 providing both mechanical stimulation therapy as well as electrical stimulation therapy as indicated. However, it will be understood that one of ordinary skill could readily construct other embodiments of the device 400 having a subset of the components and functionality of this embodiment, such as for a device 400 lacking the electrical stimulation capability. Thus, in one embodiment, as shown in FIG. 7, a medical therapy device 400 comprising an implantable cardiac stimulation device is in electrical communication with a patient's heart 12 by way of three leads, 20, 24 and 30, suitable for delivering multi-chamber stimulation and shock therapy. To sense atrial cardiac signals and to provide right atrial chamber stimulation therapy, the therapy device 400 is coupled to an implantable right atrial lead 20 having at least an atrial tip electrode 22, which typically is implanted in the patient's right atrial appendage.

To sense left atrial and ventricular cardiac signals and to provide left chamber pacing therapy, the therapy device 400 is coupled to a "coronary sinus" lead 24 designed for placement in the "coronary sinus region" via the coronary sinus ostium (OS) for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/ or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The therapy device 400 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 8:
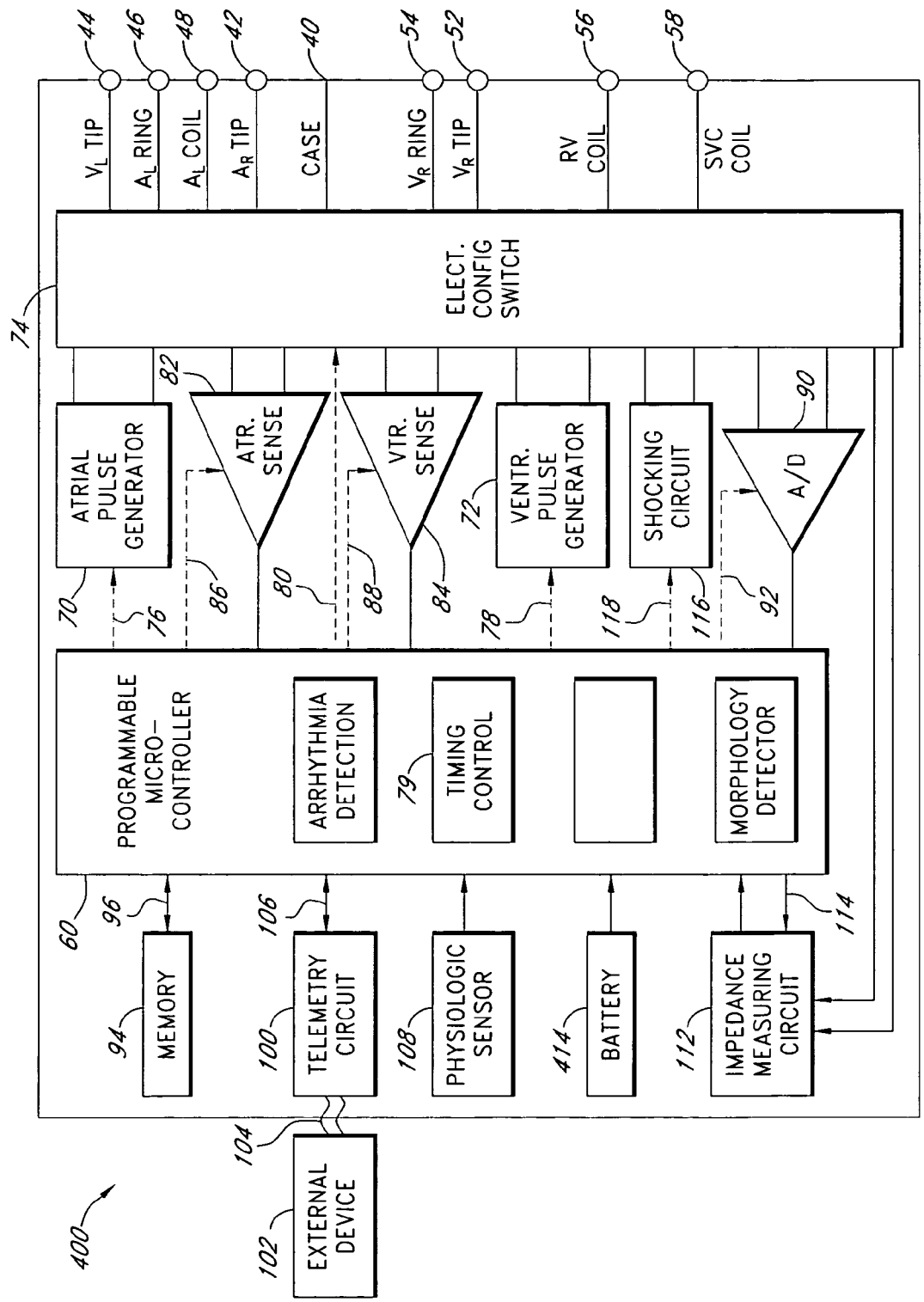
FIG. 8 is a functional block diagram of the multi-chamber implantable stimulation device aspects of the embodiment of FIG. 7 illustrating the basic elements of a stimulation device which can provide cardioversion, defibrillation and pacing stimulation in four chambers of the heart.

As illustrated in FIG. 8, a simplified block diagram is shown of the device 400, which is capable of treating both fast and slow arrhythmias with multi-chamber stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the therapy device 400, shown schematically in FIG. 8, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the therapy device 400 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 8, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independently of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 400 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 400 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (ND) data acquisition system 90. The data acquisition system 90 is configured to acquire intracardiac electrogram (IEGM) signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the therapy device 400 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 400 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows IEGMs and status information relating to the operation of the device 400 (as contained in the microcontroller 60 or memory 94) to be sent to the external device 102 through an established communication link 104.

In the preferred embodiment, the therapy device 400 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses. In certain embodiments, the physiologic sensor 108 also comprises a pressure/acoustic sensor such that the physiologic sensor 108 can develop mechanically based determinations of the heart rate and/or blood pressure for determination of delivery of mechanical therapy as well as electrical stimulation.

The therapy device 400 additionally includes a battery 416 which provides operating power to all of the circuits shown in FIG. 8. For the therapy device 400, which employs shocking therapy, the battery 416 must be capable of operating at low current drains for long periods of time and then be capable of providing high-current pulses (for capacitor charging) when the patient requires a shock pulse. The battery 416 must also have a predictable discharge characteristic so that elective replacement time can be detected. Accordingly, the device 400 in preferred embodiments employs lithium/silver vanadium oxide batteries.

As further shown in FIG. 8, the device 400 is shown as having an impedance measuring circuit 112 which is enabled by the microcontroller 60 via a control signal 114.

In the case where the therapy device 400 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Again as previously noted, one of ordinary skill can construct a device 400 employing a subset of the above described features and components, such as a device 400 lacking the electrical stimulation capability and wherein the hybrid electronics 406 comprises a subset of the components and functionality to support the mechanical therapy delivery described above without the electrical stimulation therapy.

Figure 9:
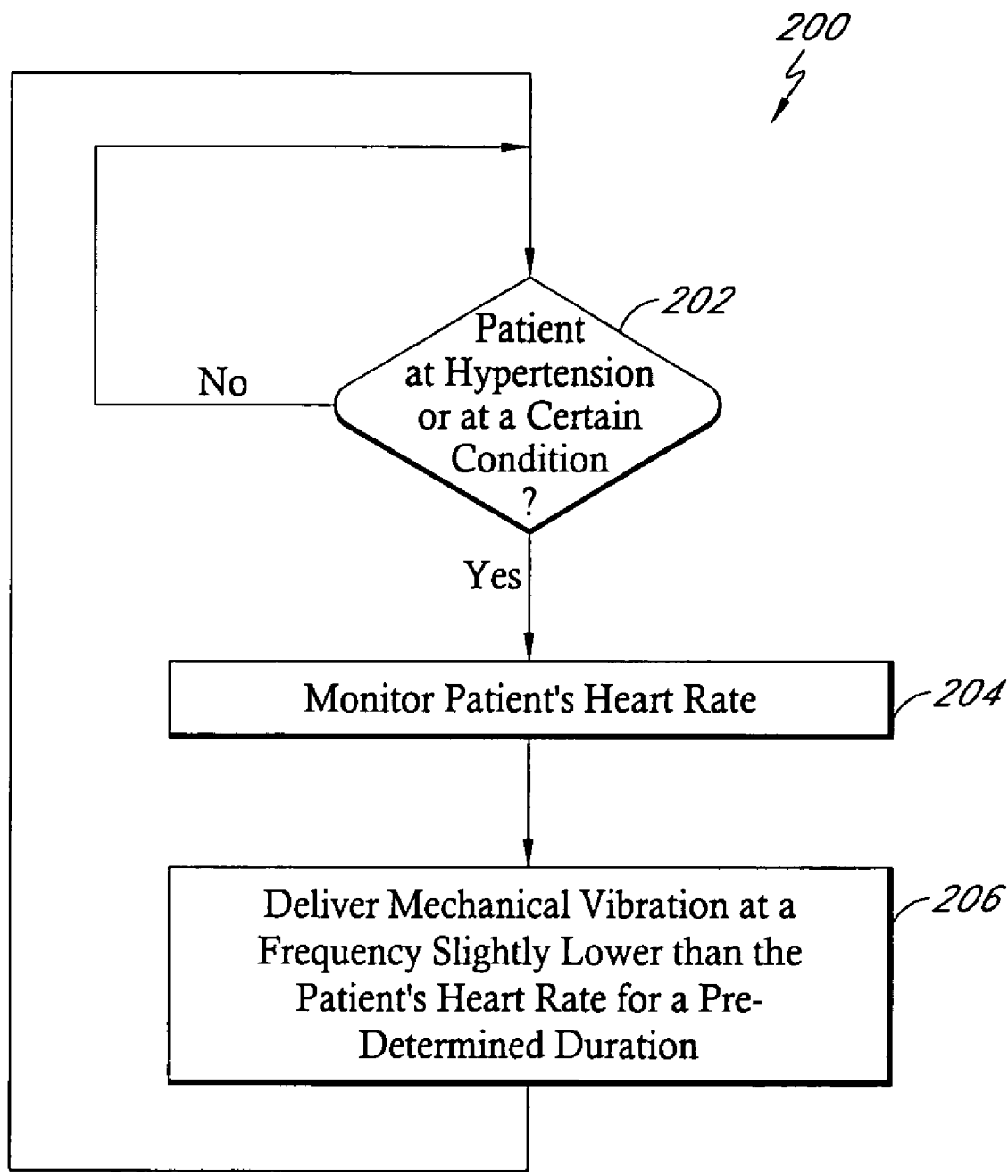
FIG. 9 is a flow chart of one embodiment of determining and delivering therapy directed generally to hypertension.

FIG. 9 is a flow chart illustrating one embodiment of a method of providing medical therapy 200. In certain embodiments, the method 200 would be performed on a long term, ongoing, or chronic basis, and in other embodiments is employed on a short term or acute basis as indicated. The method 200 begins with a decision state 202 wherein an evaluation is made as to whether the patient is experiencing a condition indicating medical therapy. The decision of 202 is in certain embodiments made by a clinician following standard examination and testing procedures and in other embodiments is made in addition or alternatively in an automatic manner following monitoring of the patient. This embodiment of the method 200 is directed generally towards evaluation and treatment of hypertension conditions, however, in other embodiments, other patient conditions can be effectively treated with the method 200 described. Further explanation of this embodiment will be made with respect to hypertension for brevity and ease of understanding.

If a condition is not observed which would indicate medical therapy, the method 200 continues to make the evaluation of state 202 in case such a condition arises. Upon determination that a condition does exist indicating delivery of medical therapy, the method 200 proceeds to a state 204 wherein the patient's heart rate is monitored. The monitoring of the patient's heart rate of 204 can be performed in a variety of known manners, such as detection of electrical signals arising from the cardiac activity such as an intracardiac electrogram (IEGM) and/or a surface electrocardiogram (ECG). In other embodiments, the monitoring of state 204 can follow from acoustic or direct pressure transducers, such as the physiologic sensor 108, which can be either affixed to the patient's body and/or implanted therein.

Following the monitoring of the patient's heart rate of state 204 follows a therapy delivery state 206 wherein mechanical vibrations are generated and delivered to tissue of the patient at a different frequency than the observed heart rate from state 204 for a determined duration. The mechanical vibration provides spatial perturbations or displacements which are generally cyclical in nature. These vibrations are provided to emulate reflected wave energy from the patient's arterial system. The vibrations are directed to provide a supplemental feedback mechanism to the patient's cardiac system to induce the heart to raise or lower the rate at which it beats. Thus, the therapy delivery of state 206 comprises a mechanical stimulation of the patient's tissue which propagates throughout the body, including to the heart 12, but which is indirect in nature, e.g., is not direct electrical stimulation of tissue, such as the cardiac tissue. The mechanical stimulations act in an indirect manner to steer the patient's heart rate and/or blood pressure towards desired values.

In certain embodiments, the therapy delivery of state 206 is provided in a generally strictly periodic manner at a generally symmetric and consistent period, e.g., in a generally sinusoidal manner. In other embodiments, the mechanical vibration provides spatial perturbations or displacements from a set point which are not strictly periodic and/or symmetric in manner, e.g., excursions in opposing directions can occur at asymmetric intervals. In yet other embodiments, the mechanical vibrations are provided with greater high frequency components, such as substantially in a square-wave or saw-tooth waveform. Thus, in various embodiments, the therapy delivery of state 206 can occur in a manner that more accurately tracks actual physiological processes. Thus, use of the terms "frequency", "cyclical", and "vibration" herein does not require that the stimulation component have strictly periodic characteristics, e.g., sinusoidal in nature, and is intended to encompass a variety of complex wave-form and movement characteristics as well as more simple sinusoidal wave forms and movement characteristics.

The delivery of therapy of state 206 in certain preferred embodiments is at a frequency slightly lower than the observed native or intrinsic heart rate from state 204. The particular rate at which the therapy is delivered in state 206 can be programmed by a clinician in accordance with the particular needs of the individual patient. It has been found that improved efficacy of the method 200 is found when the rate of mechanical stimulation provided in state 206 is within approximately 20% of the patient's native heart rate from state 204. In preferred embodiments, it has also been found that increased efficacy of the method is found when the therapeutic stimulation of state 206 is provided for at least a predetermined duration generally in the range of approximately 10 minutes or more. Of course in certain embodiments the therapeutic stimulation of state 206 can be provided for extended periods of time such as for chronic heart rate and/or hypertension therapy depending on the indications for the particular patient.

Figure 10:
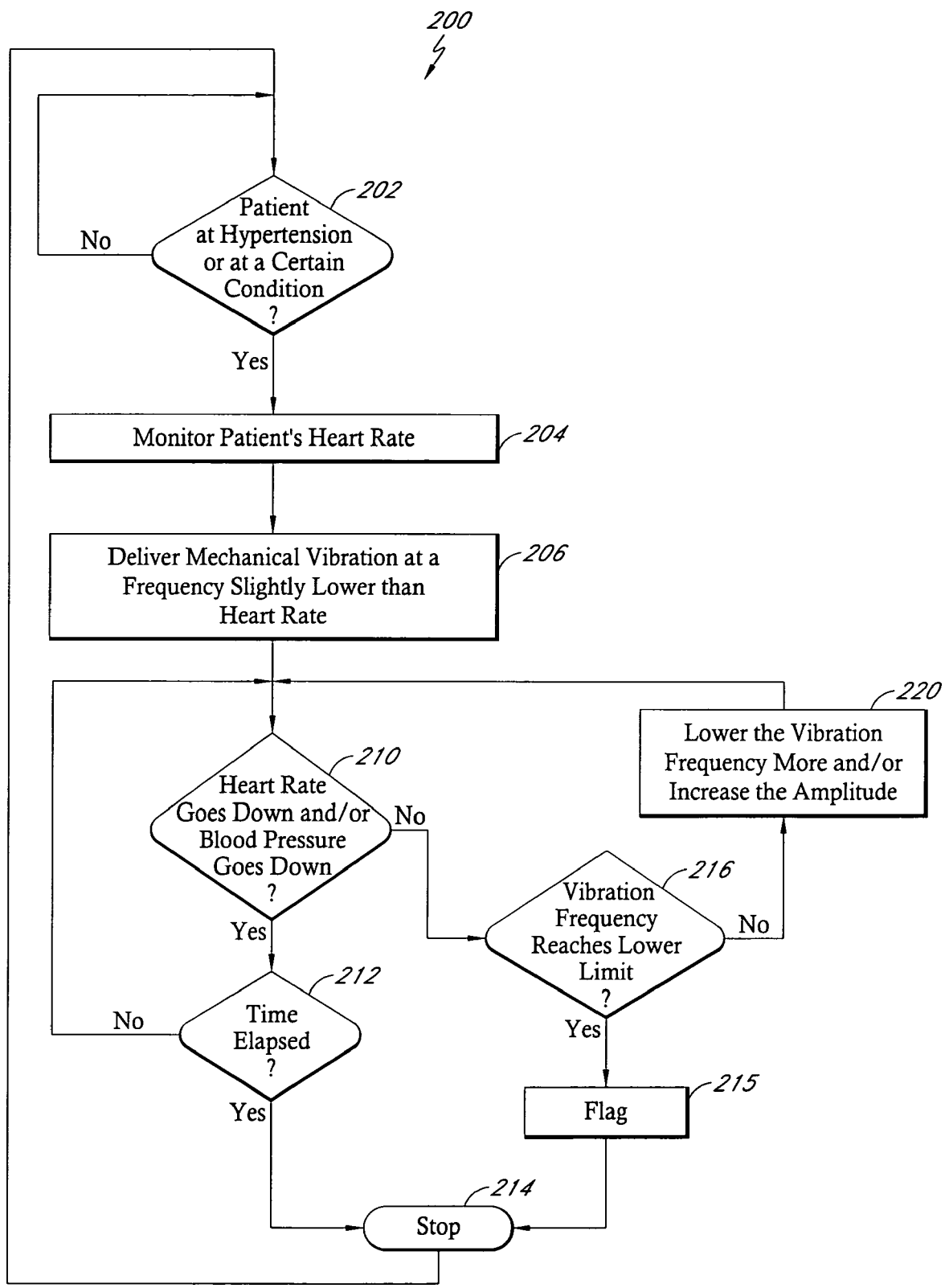
FIG. 10 is a flow chart of a further embodiment of determining and delivering therapy directed generally to hypertension.

FIG. 10 is a flow chart illustrating further embodiments of a method of determining and delivering medical therapy 200. State 202, 204 and 206 are substantially as previously described and will not be repeated here. Following state 206 is a further evaluation state 210 wherein a determination is made whether a patient's heart rate has gone down and/or whether the blood pressure has gone down as desired. In various embodiments, the determination of state 210 can comprise a determination as to whether or not the heart rate and/or blood pressure has gone down by a discrete amount, a determined percentage and/or to within a threshold window of a desired value.

If the desired heart rate and/or blood pressure as determined by state 210 has been reached, a decision state 212 follows wherein a determination is made as to whether a determined period of time has elapsed. State 212 provides the facility, in this embodiment, to provide an accommodation period to provide a period for the patient to become accustomed to the new lowered heart rate and/or blood pressure and the delay of state 212 provides a period before a successive state 214 where the mechanical stimulation of state 206 is ceased to inhibit a relapse or return to the previously observed undesired condition of state 202. As previously noted, in certain embodiments the therapy of state 206 can be provided for an extended time and the period of time evaluated for in state 212 can be until the patient's next clinical examination, e.g. a period of months where the clinician can determine the continuation or revision of the patient's therapy.

If the determination of state 210 is that the heart rate and/or blood pressure has not gone down to a desired degree, a state 216 follows wherein a determination is made as to whether the intensity of mechanical vibration has reached a determined lower limit. If the lower limit of state 216 has not been reached, a state 220 follows wherein the frequency or rate of delivery of the mechanical stimulation of state 206 is lowered further to provide a stronger stimulus to lower the heart rate and/or blood pressure. In other embodiments, state 220 comprises an increase in the amplitude/energy delivered in order to provide a stronger stimulus. The stronger stimulus in this embodiment can be at the same or also at a lower frequency. If in state 216 the lower limit has been reached, state 214 ceases the therapeutic stimulation and in certain embodiments a flag is set in a state 215 to indicate that the lower limit of intensity of mechanical stimulation of state 206 was reached without a corresponding desired decrease in the heart rate and/or blood pressure. The flag of state 215 can be accessed or automatically provided for further clinical evaluation and/or consideration of alternative therapies, such as via the telemetric link 104.

Figure 11:
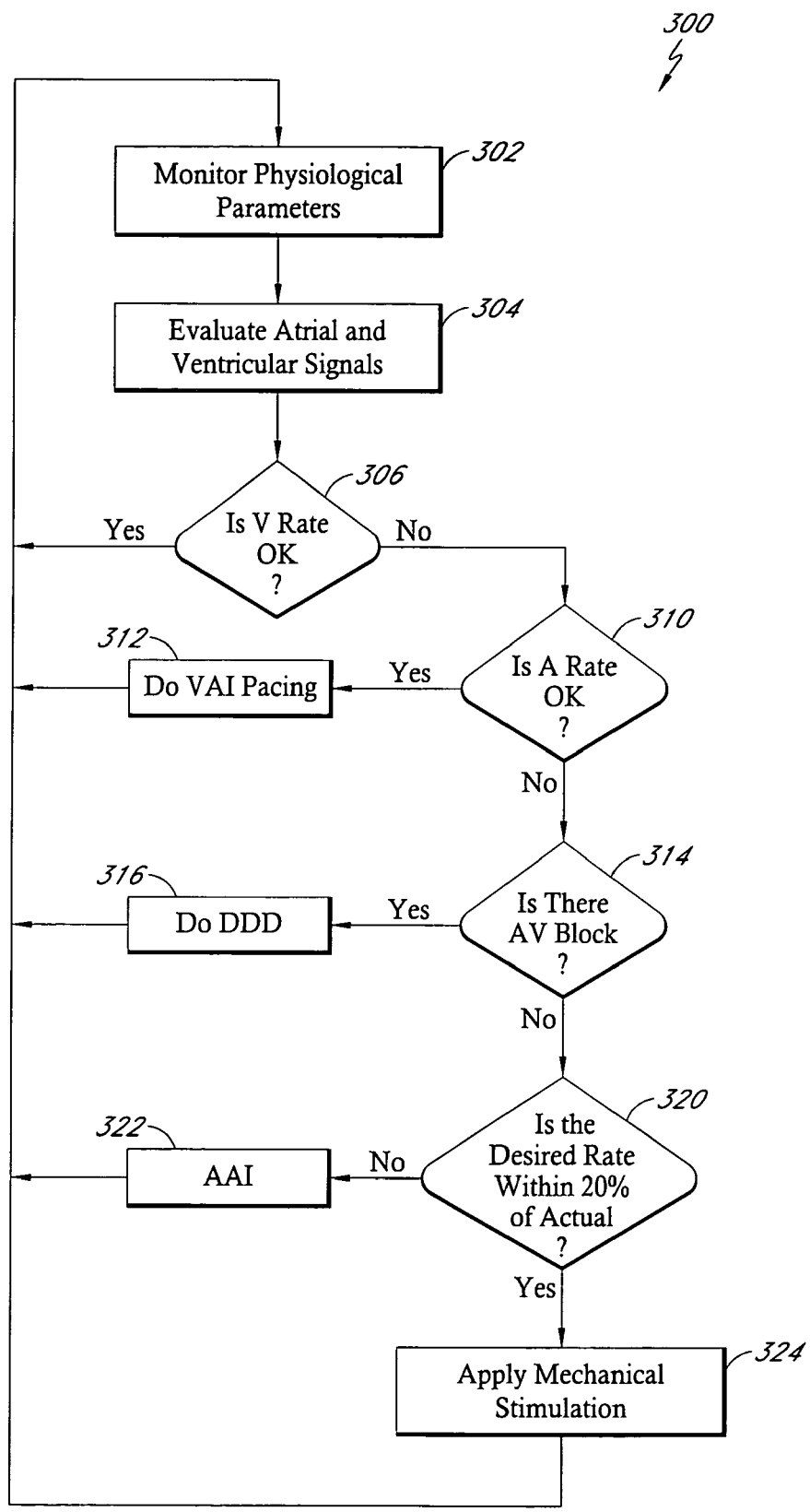
FIG. 11 is a flow chart of one embodiment of determining and delivering therapy directed generally to hypertension as well as cardiac arrhythmia.

FIG. 11 is a flow chart of an alternative embodiment of a method of determining and delivering medical therapy 300. Embodiments of the method 300 are directed generally to determining and providing therapeutic stimulation for observed conditions of cardiac arrhythmia and it will be appreciated that the embodiments of the method 300 can be provided independently as well as in combination with the embodiments of the method 200 as previously described.

Beginning in a state 302, one or more physiological parameters of the patient are monitored, such as via voltage sensors, pH sensors, pressure transducers, temperature sensors, accelerometers, etc. (108 in FIG. 8) which may be implanted or affixed to the patient as appropriate depending upon the particular application. In one particular embodiment, state 302 includes monitoring atrial and ventricular activity. Following in state 304, arterial and ventricular signals are evaluated to determine the activity in at least one each of arterial and ventricular chambers of the heart 12.

In state 306, a determination is made as to whether the observed ventricular rate is within a determined threshold of a desired value. If the ventricular rate is satisfactory, state 306 leads to a repeat of states 302, 304, and 306 for determination of a possible negative result of state 306.

If a negative determination of state 306 is made, e.g., that the ventricular rate is not satisfactory, a determination is made in state 310, whether the arterial rate is within a determined threshold of a desired value. If the determination of state 310 is affirmative, a state 312 follows wherein VAI pacing is provided to attempt to restore satisfactory ventricular rate. If the determination of state 310 is negative, a decision state 314 follows wherein a determination is made as to whether an AV block exists. If the determination of state 314 is that an AV block is present, a state 316 follows wherein DDD pacing is provided. If the determination of state 314 is negative, a decision state 320 follows wherein a determination is made as to whether the desired ventricular rate is within a threshold, in one particular embodiment 20%, of the observed ventricular rate from state 304. If the determination of state 320 is that the desired ventricular rate varies more than the threshold from the actual ventricular rate, a state 322 follows wherein AAI pacing is provided. If the determination of state 320 is that the desired ventricular rate varies by no more than the threshold from the observed ventricular rate, a state 324 follows wherein therapeutic mechanical stimulation is provided to attempt to restore the ventricular rate to the desired value. It will be appreciated that both the observed rate as well as the desired rate can vary depending on the patient's status, such as activity level and medication dosing, and that in certain embodiments the desired rate and determinations made in the method 300 based on this rate varies in a rate responsive manner.

Figure 12:
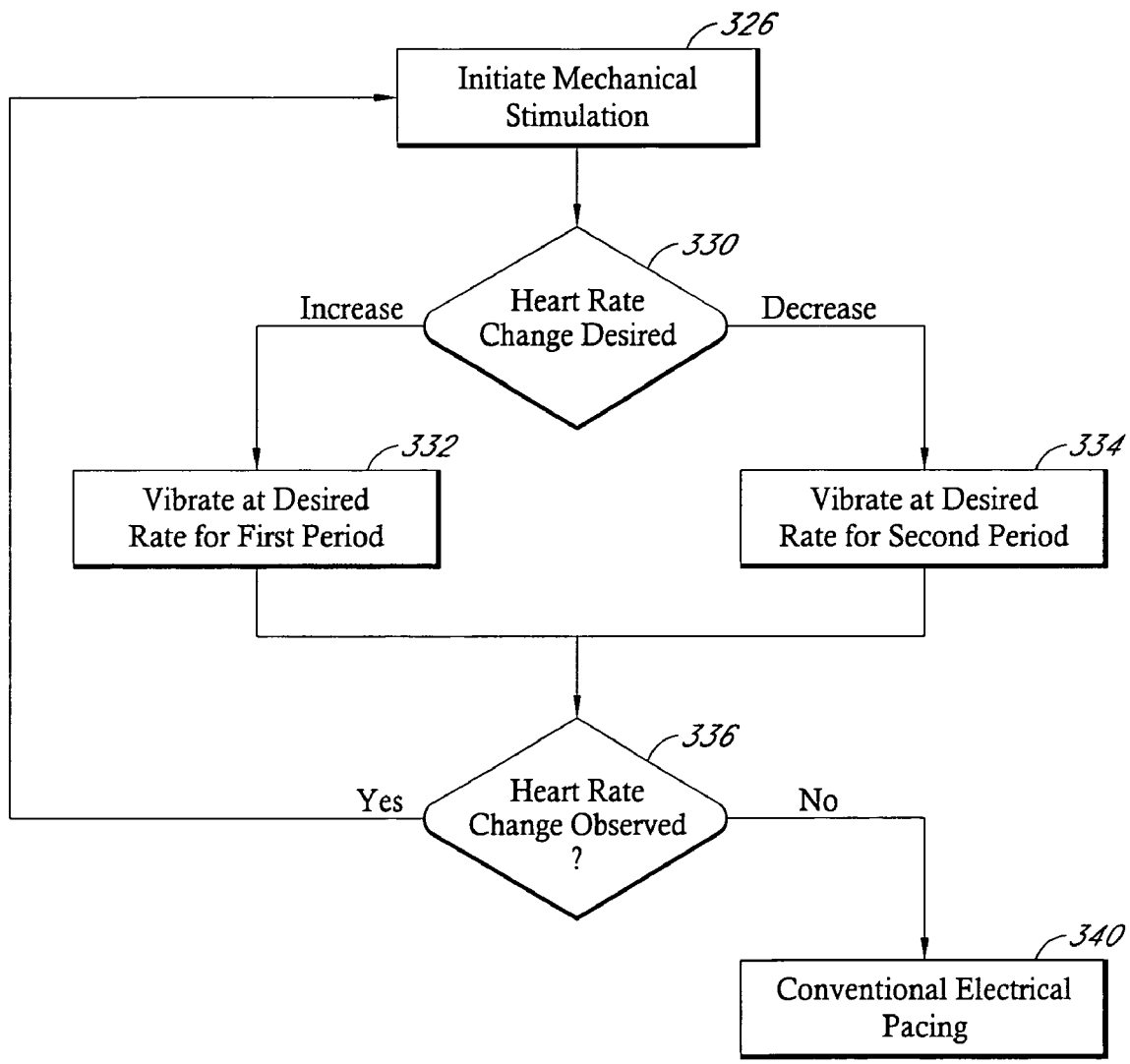
FIG. 12 is a flow chart of a further embodiment of the embodiment illustrated by FIG. 11.

FIG. 12 is a flow chart illustrating in further detail one embodiment of the state 324. The state 324 comprises a therapeutic intervention provided in selected circumstances to provide indirect mechanical stimulation to the patient to attempt to restore desired function while avoiding direct electrical stimulation of the cardiac tissue in the selected circumstances so as to reduce possible negative consequences of the electrical stimulation and to provide a more natural feedback stimulus. Thus, in this embodiment, state 324 begins with the initiation of mechanical stimulation of state 326. The mechanical stimulation of state 326 is substantially similar to that previously described with respect to embodiments of the method 200. Following initiation of the mechanical stimulation in state 326, a decision state 330 follows wherein a determination is made as to whether the change in heart rate desired is an increase or a decrease.

If the change in heart rate desired determined in state 330 is an increase, a state 332 follows wherein the mechanical stimulation or vibration is provided at the desired rate for a first period. If the determination of state 330 is that a decrease is indicated, a state 334 follows wherein the vibration of mechanical stimulation is provided at the desired rate for a second period. As in many applications it has been found that decreasing the heart rate can take a longer period of therapy delivery than to increase the heart rate, in preferred embodiments, the first period is generally shorter than the second period. In one particular embodiment, the first period comprises an interval of approximately two minutes and the second period comprises an interval of approximately ten minutes.

Following either of state 332 or state 334, a decision state 336 follows wherein a determination is made as to whether a change in observed heart rate has been observed. In certain embodiments, the evaluation of state 336 comprises an arbitrary evaluation as to whether the heart rate is within a determined threshold of the desired rate. In other embodiments, the evaluation of state 336 comprises a less stringent evaluation as to whether the observed heart rate has changed in the desired direction and thus the provision of the mechanical stimulation of state 326 at the rate and period of either of state 332 or 334 may be repeated one or more times in an iterative manner of state 324 of the method 300. If the determination of state 336 is negative, e.g., that the heart rate has not reached a desired threshold window after one or more repetitions of the state 324, a state 340 follows wherein conventional electrical pacing is provided. The various indications for delivering electrical pacing are well known in the art and will not be repeated here.

Figure 13:
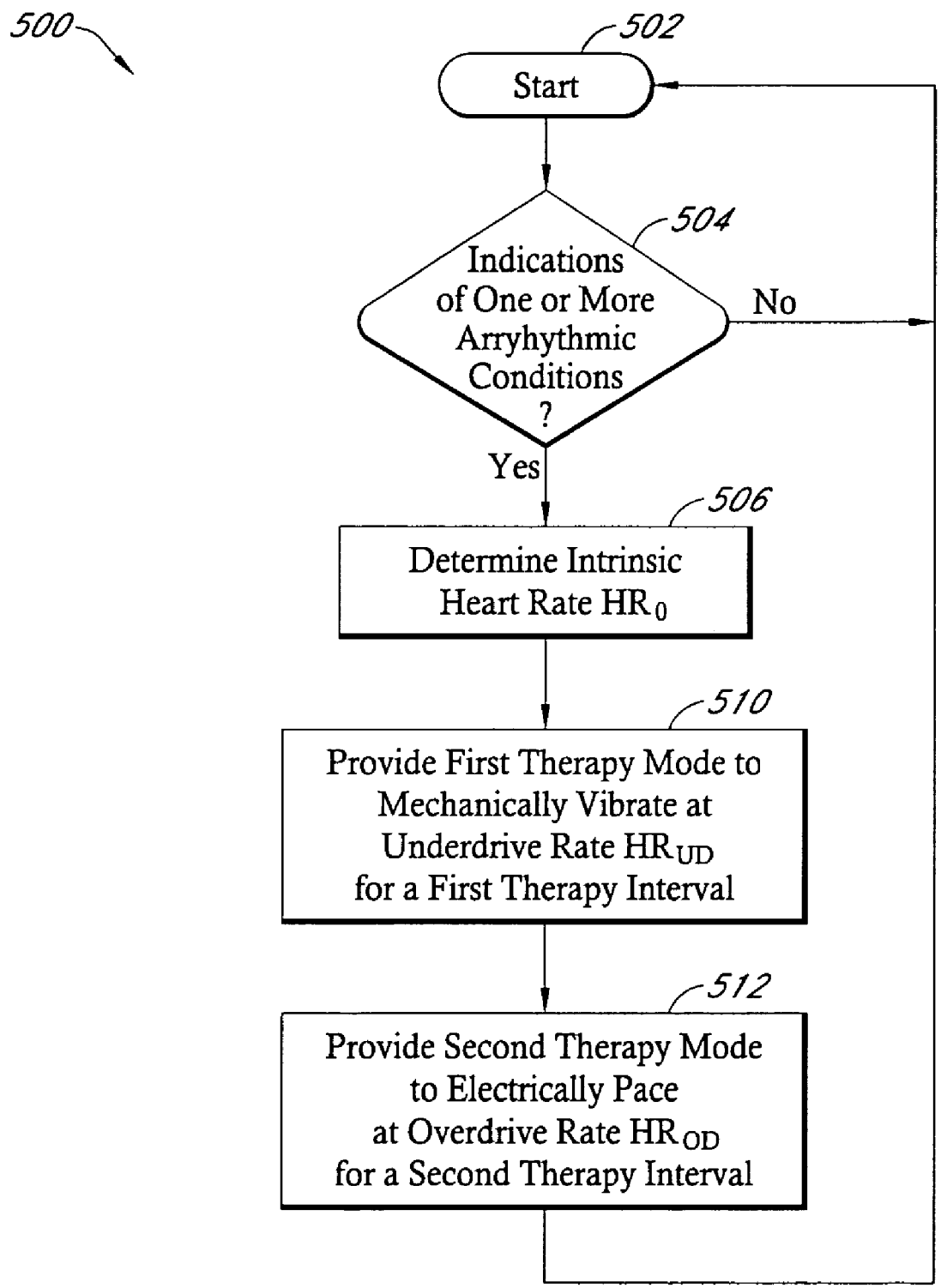
FIG. 13 is a flow chart of another embodiment of combined mechanical and electrical stimulation therapy.

FIG. 13 illustrates yet another embodiment of a system and method 500 for delivering therapy via an implantable device 400. This embodiment of system and method 500 employs the embodiments of the device 400 including both the mechanical stimulation as well as the electrical stimulation capabilities previously described. The method 500 begins in a start state 502 which generally includes the previously described ongoing monitoring and selective delivery of therapy for one or more cardiac arrhythmia conditions. These previously described processes and operations would typically be conducted on an ongoing manner and thus the following description of the method 500 would typically proceed in parallel or coincident with the other previously described operations and processes of the device 400.

Proceeding from the start state 502, a decision state 504 follows wherein a determination is made as to whether indications of certain arrhythmias are present. In certain embodiments, the certain arrhythmias comprise one or more of AF, premature atrial complex (PAC), and/or premature ventricular complex (PVC). The decision of state 504 is in certain embodiments performed by an attending physician following clinical observations/testing of the patient for indications of one or more of the certain arrhythmic conditions. In other embodiments, the determination of the state 504 proceeds in an automatic manner wherein the device 400 evaluates physiologic signals which are sensed, for example the previously described sensed cardiac depolarization signals, for indications of the arrhythmia(s). A number of known systems/algorithms for automatically determining indications of arrhythmias, including AF, are known such as those described in the co-owned U.S. Pat. Nos. 6,292,694 Sep. 18, 2001, 6,694,188 Feb. 17, 2004, 6,766,194 Jul. 20, 2004, and 6,775,571 Aug. 10, 2004 all of which are incorporated herein in their entireties. Of course in yet other embodiments, the determination of state 504 is made based on a combination of one or more automatic processes and clinician decision.

If the determination of state 504 is negative, e.g. that appropriate indications are not present, the system 500 returns to the start state 502 and to the previously described ongoing monitoring and selective provision of therapy as previously described. If the determination of state 504 is positive, e.g. that indications are present, the system and method 500 proceeds to a state 506 wherein a determination is made of the patient's native or intrinsic heart rate indicated $HR_0$. The system and method 500 then proceeds to a state 510 wherein mechanical stimulation or vibration is provided at a first underdrive rate indicated $HR_{UD}$. State 510 provides a first modality of treatment, in one particular embodiment mechanical stimulation, to steer or drive the intrinsic heart rate to a lower value. In one particular embodiment, the device 400 is induced to vibrate at a rate approximately 10 pulses or cycles per minute lower than the intrinsic heart rate $HR_0$. As previously described, the mechanical vibrations are provided to mimic or emulate reflected wave energy from the patient's arterial system to provide a more natural feedback control stimulus to adjust the patient's heart rate to a lower value.

In this embodiment, the system and method 500 then proceed to a state 512 wherein a second modality of stimulation is provided at an overdrive rate indicated $HR_{OD}$. In one particular embodiment, the state 512 comprises electrical arterial pacing stimulations provided by the device 400. In one embodiment, the second modality of stimulations provided in state 512 is provided at the overdrive rate $HR_{OD}$ at a rate that is substantially equal to the intrinsic heart rate $HR_0$. Thus, in this particular embodiment, the first modality of therapy provided in state 510 artificially underdrives the patient's intrinsic or native heart rate to a lower value than the pre-existing intrinsic rate. The second modality of stimulation provided in state 512 can then artificially elevate or overdrive this new intrinsic rate to a "elevated" value, but which is substantially the same as the preexisting intrinsic heart rate $HR_0$.

Thus, the system and method 500 can effective overdrive the heart 12 via electrical stimulations (as in state 512), but such that the resulting heart rate is substantially the same as the preexisting intrinsic heart rate $HR_0$ prior to initiation of therapy. Thus, as the overdriven heart rate is substantially the same as the pre-existing intrinsic heart rate $HR_0$, the patient is much less likely to experience the irritability of an elevated heart rate as the resulting heart rate from the therapy of the system and method 500 is substantially the same as the otherwise pre-existing intrinsic heart rate HR0. However, as the electrical stimulation therapy provided by state 512 does constitute an overdrive pacing therapy, the patient can realize the benefits of the overdrive pacing, such as in suppressing further episodes of AF, PAC, and/or PVC with significantly reduced impact of the negative side effects of conventional therapies.

In other embodiments, the stimulation rates of the underdrive stimulation HRud and the overdrive stimulation HROD are selected for a more aggressive overdrive therapy. For example, the underdrive and overdrive rates can be adjusted for a greater difference or "overdrive", but with a lower net increase in heart rate as compared to the intrinsic rate HR0. In one particular implementation, an underdrive rate HRud can be set at 10 ppm below the intrinsic rate and the overdrive rate HROD set to overdrive by 15 ppm. Thus, the net result experienced by the patient is a heart rate of only +5 bpm with associated lower negative side effects but under more aggressive overdrive conditions of +15 ppm.

Figure 14:
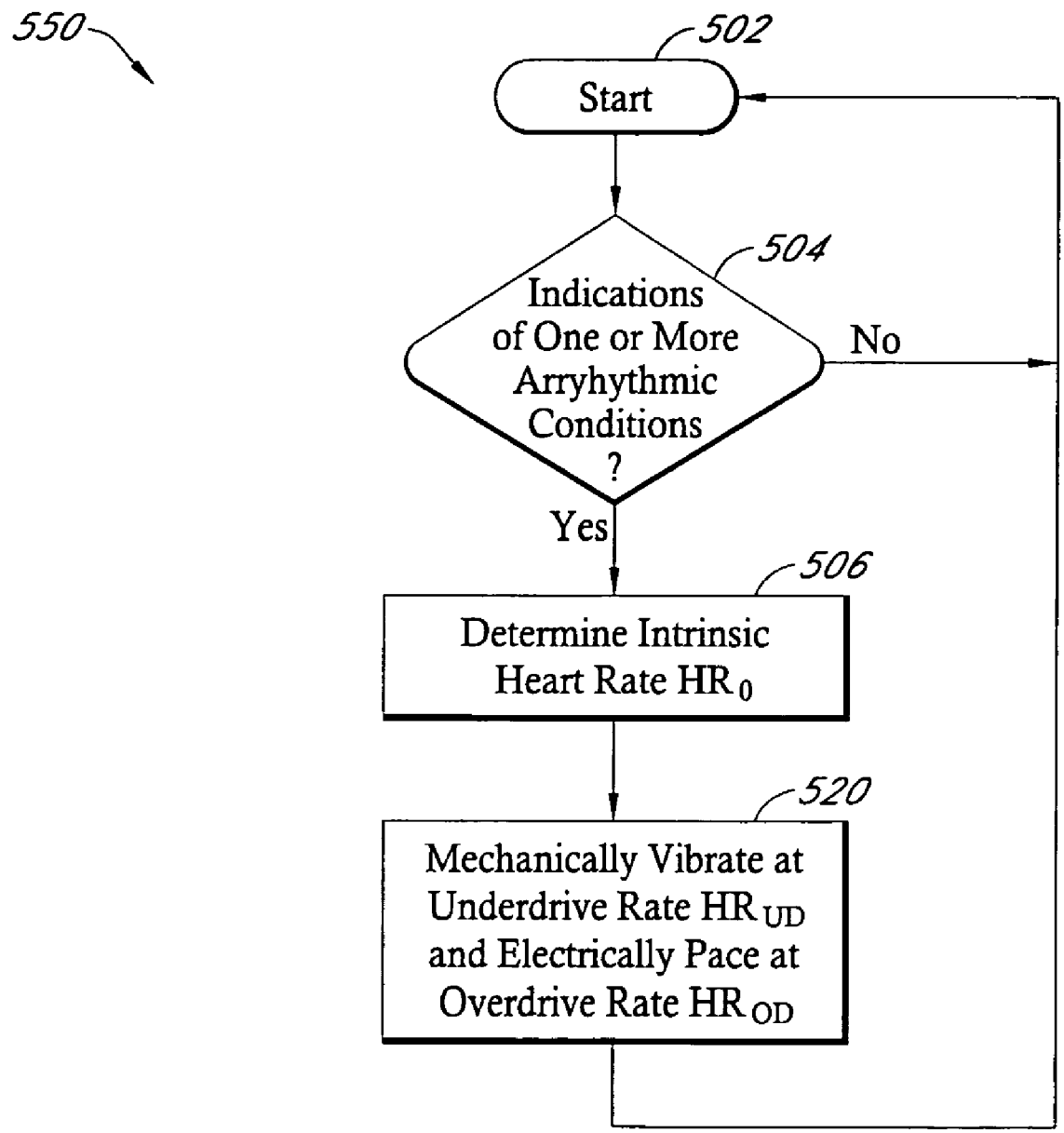
FIG. 14 is a flowchart of yet another embodiment of providing mechanical and electrical stimulation therapy in combination.
Figure 15:
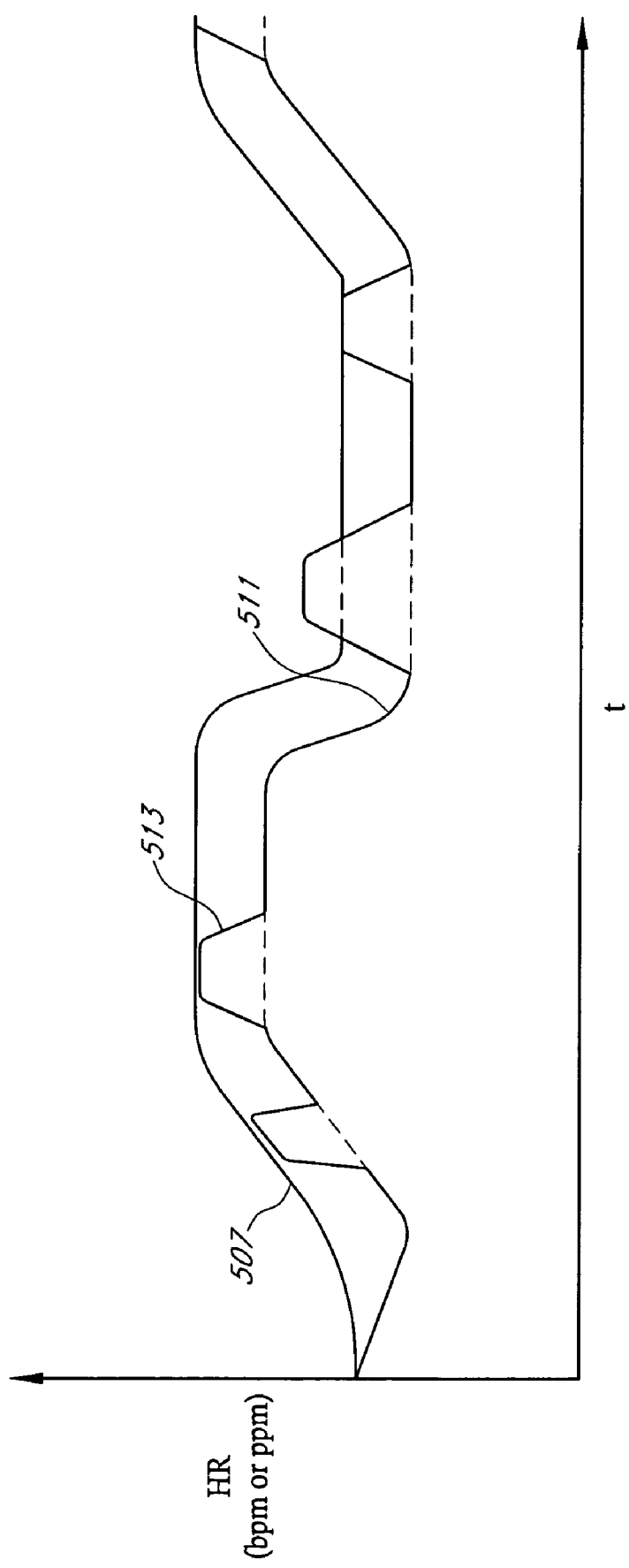
FIG. 15 is an exemplary graph of a patient's heart rate when provided therapy according to certain embodiments of the invention.

FIG. 14 illustrates yet another embodiment of a system and method 550 for delivering multiple modes of stimulation therapy. The embodiment illustrated in FIG. 14 is partially similar to the system and method 500 previously described with reference to FIG. 13 and states 502, 504, and 506 proceeds substantially as previously described. Following state 506, in this embodiment, a state 520 proceeds wherein multiple stimulation modes are provided in an at least partially overlapping or simultaneous manner. In one particular embodiment, in state 520 the device 400 is induced to provide mechanical vibrations or stimulations at an underdrive rate $HR_{UD}$ as well as to provide electrical pacing stimulations at an overdrive rate $HR_{OD}$. The relative timing of the underdrive and overdrive provided by the device 400 is such that the multiple modes of therapy are at least partially concurrent. Thus, in this embodiment, the opposing multiple modes of therapy are not wholly separated in time.

Thus, in this embodiment, the device 400 initiates mechanical stimulations to lower the heart rate while at the same time providing electrical stimulations to overdrive the heart to affect the dynamic atrial overdrive (DAO) therapy. Thus, in contrast to the embodiment of the system and method 500 wherein the mechanical or first stimulations are provided in state 510 and followed sequentially by delivery of second or electrical stimulation therapy in a state 512, in this embodiment, in state 520 both the first and second modes of therapy e.g., mechanical vibration and electrical stimulation are provided in a parallel or overlapping manner.

For both the embodiments of system and method 500, 550 as illustrated in FIGS. 13 and 14, in order to extend better life while providing effective paroxysmal AF therapy, the provision of therapy in states 510 and 512 or in state 520 would typically proceed for a treatment interval and then cease for a recovery or accommodation interval with a return to the decision state 504. In certain embodiments, the duration of the treatment intervals is programmable and can constitute a preset duration or a variable duration based at least in part on the indications of AF considered in state 504. It will be also understood that the particular durations or treatment intervals of states 510 and 512 or 520 may vary between the first treatment mode therapy and the second treatment mode. In general, however, the mechanical vibration would be provided for a period of approximately ten minutes before and after the provision of the electrical stimulation therapy.

It will also be understood that the particular parameters of the underdrive rate $HR_{UD}$ and overdrive rate $HR_{OD}$ need not be selected such that the resulting post therapy heart rate is substantially equal to the pretreatment intrinsic heart rate $HR_0$. For example, in certain implementations, the underdrive rate $HR_{UD}$ is provided at a greater margin or difference from the intrinsic heart rate $HR_0$ than the margin or difference of the overdrive rate $HR_{OD}$ such that the overall resultant post therapy heart rate is lower than the intrinsic heart rate $HR_0$ while still providing the therapeutic benefits of the DAO therapy. In yet other embodiments, a first therapy mode comprising mechanical vibrations is provided subsequently to a second therapy mode comprising electrical stimulation.

Although the above disclosed embodiments of the present teachings have shown, described and pointed out the fundamental novel features of the invention as applied to the above-disclosed embodiments, it should be understood that various omissions, substitutions, and changes in the form of the detail of the devices, systems and/or methods illustrated may be made by those skilled in the art without departing from the scope of the present teachings. Consequently, the scope of the invention should not be limited to the foregoing description but should be defined by the appended claims.

What is claimed is:

1. An implantable cardiac stimulation device comprising:
a mechanical stimulation component operative to provide mechanical stimulation to a patient's heart;
an electrical stimulation component including an implantable electrical pulse generator and at least one electrode adapted to be implanted within the patient and connected to the electrical pulse generator so as to provide electrical stimulation to the heart of the patient;
at least one sensor that senses a parameter indicative of function of the patient's heart; and
a controller that uses signals from the at least one sensor to determine an untreated intrinsic heart rate corresponding to the patient's heart rate prior to provision of mechanical stimulation, the controller programmed to induce the mechanical stimulation component to provide mechanical stimulation at a first rate derived from the untreated intrinsic heart rate, and the electrical stimulation component to provide electrical stimulation at a second rate derived from the untreated intrinsic heart rate.

2. The device of claim 1, wherein the at least one sensor comprises an electrical sensor arranged to measure cardiac depolarizations and provide signals to the controller such that the controller can determine a current heart rate of the patient.

3. The device of claim 2, wherein the controller induces the mechanical stimulation component to provide stimulation to the heart at the first rate to adjust the treated intrinsic heart rate to a lower value than the untreated intrinsic heart rate.

4. The device of claim 3, wherein the first rate is approximately 10 cycles per minute below the untreated intrinsic heart rate and wherein the electrical stimulation is provided at the second rate approximately equal to the untreated intrinsic heart rate.

5. The device of claim 1, further comprising a housing and wherein the mechanical stimulation component is also adapted to be implanted within the patient and is located with the electrical pulse generator and controller within the housing.

6. The device of claim 5, wherein the mechanical stimulation component induces at least a portion of the housing to move so as to provide the mechanical stimulation.

7. The device of claim 1, wherein the mechanical stimulation component comprises a displacement mechanism providing mechanical vibrations to the patient's body.

8. The device of claim 7, wherein the mechanical stimulation component comprises a motor generating rotational movement and a crankshaft assembly engaged with the motor such that the rotational movement is converted to reciprocating movement so as to provide the mechanical vibrations.

9. The device of claim 1, wherein the mechanical vibrations and the electrical stimulations are provided sequentially.

10. An implantable therapeutic medical device comprising:
means for sensing one or more physiological parameters of a patient, including a heart rate;
means for generating mechanical vibrations;
means for delivering electrical stimulations; and
means for controlling the means for generating vibrations to deliver vibrations at a first frequency derived from the intrinsic heart rate so as to drive an intrinsic heart rate towards a lower rate and for controlling the means for delivering electrical stimulations to provide electrical stimulation at a second frequency derived from the untreated intrinsic heart rate so as to drive the heart rate higher than the lower rate.

11. The device of claim 10, wherein the means for sensing comprises at least one implantable sensing electrode configured for contact with cardiac tissue and sense amplifier circuitry engaged with the at least one implantable sensing electrode.

12. The device of claim 10, wherein the means for delivering electrical stimulations comprises an implantable stimulation pulse generator connected to at least one pair of implantable stimulation electrodes.

13. The device of claim 10, wherein the means for generating mechanical vibrations comprises a motor generating rotational movement and a displacement mechanism configured to convert the rotational movement of the motor to an oscillating movement.

14. A method of providing therapy comprising:
  measuring at least one parameter indicative of a patient's cardiac activity;
  evaluating the at least one parameter to determine an intrinsic heart rate and for indications of therapy delivery and, upon determining that delivery of therapy is indicated:
    inducing an implanted mechanical stimulator to deliver mechanical vibrations to the patient's body at a first rate derived from the intrinsic heart rate so as to lower the intrinsic heart rate; and
    inducing an implantable electrical pulse generator to deliver electrical stimulations at a second rate derived from the intrinsic heart rate so as to increase an effective heart rate above the intrinsic rate.

15. The method of claim 14, wherein the electrical stimulations and mechanical vibrations, in combination, drive the patient's effective heart rate to a rate approximately equal to or less than a pre-therapy intrinsic heart rate.

16. The method of claim 14, wherein the mechanical vibrations are provided for a first interval and the electrical stimulations are provided for a second interval.

17. The method of claim 14, wherein the mechanical vibrations and the electrical stimulations are provided sequentially.

18. The method of claim 14, wherein the mechanical vibrations and the electrical stimulations are provided at least partially simultaneously.

19. A method of treating cardiac arrhythmias comprising driving an intrinsic heart rate lower via a first stimulation modality delivered at a rate derived from the intrinsic heart rate and driving the heart rate resulting from delivery of the first stimulation modality higher via a second stimulation modality delivered at a rate derived from the intrinsic heart rate, wherein at least one of the first and second stimulation modalities are delivered at an implanted location.

20. The method of claim 19, wherein the first stimulation modality comprises mechanical vibrations delivered at a rate that is a predetermined amount less than the intrinsic rate.

21. The method of claim 19, wherein the second stimulation modality comprises electrical stimulation provided to a patient's heart at a rate a least equal to the intrinsic heart rate.

* * * * *